United States Patent [19]

Yau-Young

[11] Patent Number: 5,023,087
[45] Date of Patent: Jun. 11, 1991

[54] EFFICIENT METHOD FOR PREPARATION OF PROLONGED RELEASE LIPOSOME-BASED DRUG DELIVERY SYSTEM

[75] Inventor: Annie Yau-Young, Los Altos, Calif.

[73] Assignee: Liposome Technology, Inc., Menlo Park, Calif.

[21] Appl. No.: 326,198

[22] Filed: May 12, 1989

Related U.S. Application Data

[63] Continuation-in-part of Ser. No. 215,075, Jul. 5, 1988, abandoned, which is a continuation of Ser. No. 828,153, Feb. 10, 1986, abandoned.

[51] Int. Cl.$^5$ .............................................. A61K 37/22
[52] U.S. Cl. .................................. 424/450; 424/1.1; 424/9; 264/4.6
[58] Field of Search ............................ 424/450, 1.1, 9; 264/4.6

[56] References Cited

U.S. PATENT DOCUMENTS

| | | | |
|---|---|---|---|
| 4,394,448 | 7/1983 | Szoka | 424/450 |
| 4,752,425 | 6/1988 | Martin et al. | 424/450 |
| 4,837,028 | 6/1989 | Allen | 424/450 |
| 4,873,088 | 10/1989 | Mayhew et al. | 424/450 |

FOREIGN PATENT DOCUMENTS 2050287A  5/1980  United Kingdom .

OTHER PUBLICATIONS

Chemical Abstract, 99:58815, (1983).
Fukunaga, M. et al., Endocrinology, 115(2):757, (1984).
Jackson, A. J., Drug Metabolism and Disposition, 9(6):535, (1981).
McFarlane, A. S., Nature, 182(4627):53, (1958).
Szoka, F., Jr., Ann. Rev. Biophys. Bioeng., 9:467, (1980).
Szoka, F., Jr., Proc. Nat. Acad. Sci., U.S.A., 75:4194.
Abra, R. M. et al., Research Communications, 36(1):17-31, (1982).
Abra, R. M. et al., Research Communications in Chemical Pathology and Pharmacology, 36(1):17-31, (1982).
Greenwood, F. C., et al., Biochem. J., 89:114, (1963).
Chu Hua Kang et al., IRCS Medical Science: Alimentary System: Anatomy and Human Biology; Biochemistry; Biomedical Tech., 11:420-421, (1983).
Abra, Robert M. et al., "Liposome Disposition In Vivo: Effects of Pre-Dosing with Liposomes", School of Pharmacy, UCSF, 29(2):349-360, (1980).
Juliano, R. L., et al., in *Biochemical and Biophysical Research Communications*, 63(3), "The Effect of Particle Size and Charge on the Clearance Rates of Liposomes and Liposome Encapsulated Drugs", Academic Press, Inc., (1975).

*Primary Examiner*—Thurman Page
*Assistant Examiner*—William E. Benston, Jr.
*Attorney, Agent, or Firm*—Peter J. Dehlinger; Gary R. Fabian

[57] ABSTRACT

A method for selectively controlling the rate of release of a liposome-entrapped compound from an intramuscular or subcutaneous injection site. The method includes selecting the average size, amount, and lipid composition of liposomes injected into the site to produce a desired half-life of release of the compound. A preferred composition used in practicing the invention includes an aqueous suspension of liposomes containing the compound in entrapped form, and having average particle sizes less than about 0.2 microns, and large amount of larger empty lipsomes present in an amount effective to increase the half-life of release of the compound from the injection site to a desired half-life between about 1-14 days.

13 Claims, 5 Drawing Sheets

EFFICIENT METHOD FOR PREPARATION OF PROLONGED RELEASE LIPOSOME-BASED DRUG DELIVERY SYSTEM

This application is a Continuation-in-Part of U.S. patent application Ser. No. 215,075 filed on July 5, 1988, now abandoned which is Continuation of the U.S. patent application Ser. No. 828,153 filed on Feb. 10, 1986, now abandoned.

BACKGROUND OF THE INVENTION

1. Field of the Invention

One aspect of the present invention relates to a liposome-based drug delivery system for prolonged release at a controlled rate of a pharmacologically active compound from the site of administration to the bloodstream. The novel delivery system concerns a liposomal formulation consisting of mixture of a small portion of liposomes with encapsulated drug and a large portion of empty liposomes. The formulation increases half-life of clearance from the injection site, and has the similar release kinetics as the formulation where all liposomes contain the drug. The formulation is also convenient for scale-up process.

The second aspect of the present invention relates to the extended stability of the drug encapsulated in liposomes over the free drug. Liposome encapsulation enables the storage of the drug at very low overall concentration at which the free drug would have lost its activity.

References

1. Abra, R. M., et al., *Res. Commun. Chem. Path. and Pharmacol.*, 29:349 (1980).
2. Abra, R. M., et.al., *Res. Commun. Chem. Path. and Pharmacol.*, 37:17 (1982a).
3. Abra, R. M., et al., *Res. Commun. Chem. Path. and Pharmacol.*, 37:199 (1982b).
4. Arakawa, E., et al., *Chem. Pharm. Bull.*, 23:2218 (1975).
5. Fukunaga, M., et al., *Endocrinology*, 115(2):757 (1985).
6. Greenwood, F. C., et al., *Biochem. J..* 89:114 (1963).
7. Jackson, A. J., *Drug Metab. and Dispos.*, 9(6):535 (1981).
8. McFarlane, A. S., *Nature*, 182:53 (1958).
9. Szoka, F., *Proc. Nat. Acad. Sci.*, USA, 75:4194 (1978).
10. Szoka, F., *Ann. Rev. Biophys. Bioeng.*, 9:467 (1980).

2. Background and Related Disclosures

Liposome delivery systems have been proposed for a variety of pharmacologically active compounds, such as various lipid and water soluble drugs, peptides, antibiotics and hormones. The liposomal route of drug delivery differ substantially between water and lipid soluble drugs. Some lipid soluble drugs have a high liposome permeability and are thus readily transferred through the lipid bilayer. On the contrary, most water soluble drugs have low liposome permeability and thus their transfer through the liposome lipid bilayer is very slow. For these compounds the ordinary liposome formulation would be impractical if the release could not be controlled in any reasonable fashion.

It would therefore be greatly advantageous to have available a system which would allow a controlled, prolonged release of the water soluble and/or, liposome impermeable drug from the liposomes.

For compounds which are administered parenterally, liposomes have the potential of providing controlled "depot" release over an extended time period, and of reducing toxic side effects by limiting the plasma peak level of the free compound in the bloodstream. These combined advantages allow the compound to be administered less frequently, and at a higher dose level, thereby increasing the convenience of the therapeutic regimen.

One route of liposome administration which has been widely proposed for parenteral administration is intravenous (IV) injection. Liposomes administered by this route are generally cleared very fast by the reticuloendothelial system (RES), and as a consequence, the liposomes tend to concentrate in organs, which are rich in RES cells, such as the liver, spleen, and lung. In certain instances, this ability to direct liposomes somewhat specifically to RES-rich tissue is advantageous, for example, in treating disease of the liver, spleen, or lungs. This approach is described, in U.S. Pat. No. 4,797,285 "Liposome/Anthraquinone Drug Composition and Method", issued January 10, 1989, which discloses an improved therapy for treating hepatic tumors by liposome-entrapped doxorubicin. Often however, when the compound to be administered is intended for a site other than a RES-rich tissue, for example the cytotoxic drugs intended for solid tumor treatment, IV administration is of limited use, particularly if long-term release into the bloodstream is needed and in some cases it may be even detrimental as it allows the flooding of the liver or spleen with a large amount of a relatively toxic drug.

Thus it would be advantageous to have available delivery system which would allow the prolonged release of the drug from the liposomes into the bloodstream without saturating the RES system with the excess of drugs.

Intramuscular (IM) or subcutaneous (SQ) administration of liposome-entrapped compounds have been previously proposed. This approach has the advantage that, as long as the liposomes are sterile, have low pyrogen level and are contained at the site of injection, rapid uptake and clearance by the RES cannot occur. The liposomes immobilized at the site of injection can then release the entrapped compound into the bloodstream over an extended period. By way of example, U.K. Patent Application No. 2,050,287 describes a liposome system which is intended for slow release of insulin from an SQ injection site. More recently, a system for releasing liposome-encapsulated calcitonin, a peptide hormone which lowers calcium level in blood and regulates bone growth, from an IM site of administration has been proposed by Fukunaga et al. who showed that (a) a combination of free calcitonin with empty liposomes does not prolong the hypocalcemic effect of the free drug, (b) liposomal entrapment of calcitonin potentiates the degree and duration of the hypocalcemia, and (c) the hypocalcemic effect of calcitonin is prolonged when the drug is encapsulated in multilamellar liposomes while it is less or not at all affected when the drug is encapsulated in small unilamellar vesicles.

It would be desirable, in an IM or SQ delivery system of the type just mentioned, to be able to control the rate of release of the liposome-entrapped compound from the site of injection. Prior art attempts to understand and control the variables which affect drug-release rates from the injection site have had only limited success, however.

Arakawa reported the effect of several water soluble drugs in liposome formulations on intramuscular absorption in rats. The clearance of radiolabeled drugs or markers (sucrose, inulin, cefazolin and insulin) from the intramuscular injection site was studied and the effect of increasing the proportion of cholesterol (from 17 to 71 mole percent) in the liposomes formulations on the clearance kinetics of these drugs/markers was reported. From the study, it appears that with increasing proportion of cholesterol, the relative release rates are slowed down. However, no other liposome formulation parameters such as liposome size, lipid dose are described or can be inferred.

Study reported by Jackson examined the effect of several liposome variables such as size, surface area and the amount of injected lipid dose on the release of liposome entrapped radio-labeled inulin, a water soluble liposome impermeable marker, from an intramuscular injection site of mice. From these studies, the following can be concluded: (a) small liposomes (0.15–0.7% micron) are drained more rapidly by the lymphatics than the larger liposomes (0.3–2.0 micron) at the same lipid dose: (b) at 24 hours after administration, higher percentage of inulin remained at the injection site from a formulation at a lower lipid dose of large liposomes, i.e., slower rate of release inulin from low lipid dose formulations; and (c) decreasing the total amount of lipid dose results in a slower absorption of inulin from large liposomes and a greater drainage into the lymphatics. Jackson concludes that in order to prolong the absorption of the drug from liposome formulations, large liposomes in low lipid dose should be made. This observation is to contradictory to the present invention where high lipid doses are found to slow down the release of the drug from liposomes.

The fate and uptake of liposomes after intravenously administration are entirely different from intramuscular depot of liposomes. As mentioned above, intravenously administered liposomes or any particulate matter are taken up rapidly via RES, namely, the liver and spleen. Usually, the encapsulated drug and the liposomes are removed simultaneously from systemic circulation. When a large dose of liposomes is administered, these organs may become saturated such that subsequent intravenous administration of any particulate matter will not be efficiently removed from circulation. Abra et al. (1980) reported a study of the effect of high intravenous dose (1.9 umole per 20 gm body weight) of extruded multilamellar liposomes on the subsequent ability of mouse tissues to take up a second intravenous dose of similar liposomes encapsulated radio-labeled inulin. The second liposome dose was taken up much less effectively by the liver and higher proportion of the second dose remained in circulation one hour after IV injection. However, this effect was reversed by 24 hours after the administration of the first dose. Abra et al. (1982b) further studied the pre-dosing phenomenon with respect to liposome size and shown that large liposomes (0.5 micron) are effective in achieving RES saturation for the subsequent uptake of large and small liposomes, while small liposomes (0.06 micron) are not effective even at a ten-fold higher lipid dose to saturate the RES. However, pre-dosing with small liposomes is effective in blocking the uptake of subsequent IV injection of small liposomes. All effects are reversed 24 hours after administration of the first liposome dose.

The field of this invention, i.e., intramuscular or subcutaneous delivery of liposomal drug is not applicable and cannot be compared to the intravenous route of administration since the mechanism of drug release by the intramuscular route is entirely different, i.e., the liposomes are destabilized at the intramuscular or subcutaneous injection site thereby releasing the drug into either the lymphatics or the systemic circulation. It should be noted that the prolonged drug release effect of mixing large proportion of "empty" liposomes with drug containing liposomes lasts over 1 to 14 days depending on the formulation.

The following are observations which are accepted in the art. The empty liposomes can be easily sterilized by terminal filtration if they are less than 0.3 micron or they can be made by sterile process if they are larger than 0.3 micron. Depending on the extent of drug encapsulation, the incorporation of the drug into the liposomes necessarily results in certain amount of the drug remaining free, i.e. non-encapsulated. In most instances, the free drug has to be removed from the formulation before it is suitable for medical use to provide definite and controllable drug dosage. The free drug is normally removed by step of diafiltration, ion exchange or size exclusion chromatography. Thus, to prepare a formulation of drug encapsulated in large liposomes, several additional steps, such as removal of free drug and subsequent sterilization, are necessary to obtain a pharmaceutically suitable liposome-drug mixture for prolonged release from the injection site. The preparation of empty liposomes, on the other hand, requires only sterile formation of liposomes (FIG. 1).

It would, therefore be advantageous to have available means for achieving the same prolonged release of the drug from the liposomes without needing to include any additional steps for making large quantities of the drug-containing liposomal formulation.

It is therefore a primary object of this invention to provide such means.

SUMMARY

One object of this invention is to provide a system and method for controlling in a selected manner, the rate of release of a water soluble and/or liposome-impermeable compound from an IM or SQ site.

The second object of this invention is to achieve an extended stability of the drug encapsulated in the liposomes over the free drug especially at low overall concentration of encapsulated drug.

Another object of the invention is to provide such a system which can be readily prepared in sterile form suitable for IM or SQ administration in humans.

Still another object of the invention is to provide a stable liposome water soluble and/or liposome impermeable drug composition for use in parenteral drug delivery at a controlled release rate.

Yet another object of the invention is to selectively increase the rate of release of a water soluble and/or liposome impermeable compound into the bloodstream by selectively varying the size of the liposomes, the lipid composition and the amount of lipids by diluting the encapsulated liposomes with empty liposomes or by combination of all of the above.

Still another object of the invention is to provide a liposome formulation comprising a smaller portion of liposomes with encapsulated water soluble drug and a larger portion of empty liposomes, having the substantially same prolonged release properties as the formulation comprising solely of liposomes with encapsulated drug undiluted with empty liposomes.

In still another aspect, the invention includes a liposome formulation of a hormone such as calcitonin (CT) composition comprising a sterile, aqueous suspension of liposomes containing at least about 1 to 0.1 mole percent alpha-tocopherol, and CT entrapped in the liposomes at a concentration within the encapsulation space of the liposomes of at least about 0.1-1 mg/ml. The composition may be further stabilized by the presence of ferrioxamine, in a molar excess of the amount of ferric iron in the suspension.

The final aspect of this invention includes liposome formulation of antibiotics, such as gentamicin, comprising a sterile, aqueous suspension of liposomes containing at least about 0.1 mole percent alpha-tocopherol, and gentamicin entrapped in the liposomes at a concentration at least up to 200 mg/ml within the encapsulation space of the liposomes. The composition may be further stabilized by the presence of ferrioxamine, in a molar excess of the amount of ferric iron in the suspension.

These and other objects and features of the invention will become more fully apparent when the following detailed description of the invention is read in conjunction with the accompanying drawings.

DETAILED DESCRIPTION OF THE INVENTION

Figure 1:
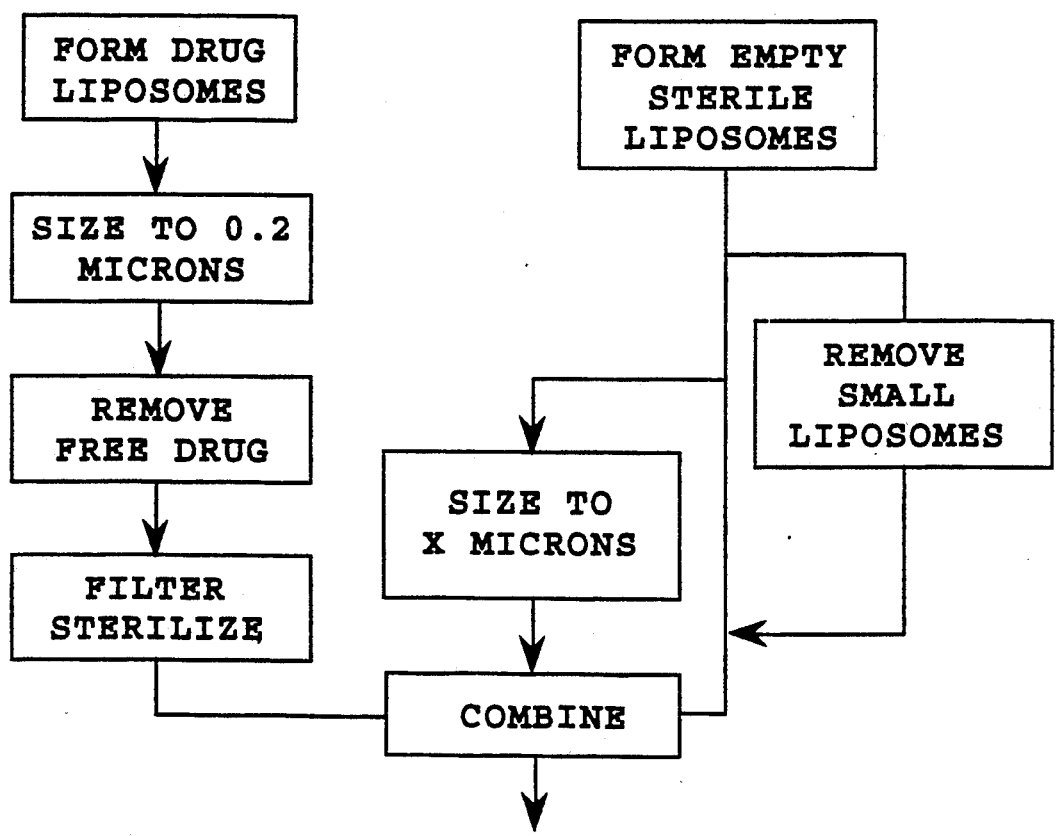
FIG. 1 is a flow diagram of a processing method used in preparing a liposome composition containing both empty and drugencapsulating lipids.

This invention concerns a novel delivery system and a method for selectively increasing the rate of release of a water-soluble liposome-impermeable compound into the bloodstream. The system consists of a liposome/-drug formulation comprising a mixture of small portion of liposomes with encapsulated drug and a larger portion of the large empty liposomes. The system is in particular useful for prolonged release of water soluble and/or not highly liposome permeable drugs from liposomes at the site of administration. However, the system can be also advantageously used for compounds which are lipid soluble but with low liposome permeability. The compound is administered by forming a suspension of liposomes containing the compound in entrapped form, and injecting the suspension into IM or SQ site. The rate of release of the agent from the site is increased selectively by increasing the average size of the liposomes and the selection of lipid composition total amount of liposome lipid injected into the site. The preferred encapsulated agent is any water soluble and-/or liposome impermeable or slightly permeable drug such as peptides, hormones, such as growth hormone and calcitonin, interferon, epidermal growth factor (EGF), immunomodulators such as interleukin-2, antibiotics such as aminoglycosides, all of which are advantageously released into the bloodstream at a controlled rate over a several day period.

The rate of release of the liposome-encapsulated agent can be controlled by the size of liposomes, total amount of lipids, or changes in the lipid composition of the liposomes. For example, negatively charged phospholipids, such as phosphatidyl-glycerol (PG), tend to increase the release rate, while the cholesterol tends to decrease the release rate.

The preferred embodiment of the current invention is the formulation wherein the liposomes are prepared by first forming a suspension of small, drug-containing liposomes, removing the free non-encapsulated compound from the suspension, filter sterilizing the suspension, then adding sterilely prepared empty liposomes to the suspension until the desired liposome drug and lipid concentrations are reached. The small liposomes are preferably less than about 0.3 microns in size, and the empty liposomes are larger than 0.5 micron.

The preferred embodiment of this invention is used for administering a water-soluble liposome-impermeable compound to the bloodstream from an IM or SQ site of injection. The embodiment is composed of an aqueous suspension of liposomes containing the substance in entrapped form, having average particle sizesless than about 0.3 microns, mixed with a quantity of empty liposomes, in an amount effective to increase the half-life of clearance of the substance from such injection site to a desired half-life between about 1-14 days. The size, lipid composition, the total lipid dose and relative quantity of empty liposomes are variably selected to produce a desired rate of release of the encapsulated agent from the site of injection.

The resulting liposomal formulation increases half-time of clearance of the drug and lipid from the injection site, has extraordinarily long stability at low drug concentration, shows the same biological activity as the formulation made of liposomes with homogeneously encapsulated drug and the preparation of large quantities is easier, quicker and very suitable for scale-up.

Definitions

As used herein:

"Small liposomes" means liposomes with sizes not exceeding 0.3 um.

"Large liposomes" means liposomes of which size is larger than 0.5 um.

"Empty liposomes" means liposomes which do not contain the active ingredient but may contain other excipients such as salts, chelating agents, antioxidants as necessary.

"MLV" means multilamellar liposomes which can have broad size ranges from 0.1 to 20 microns. MLV having size distribution of less than 0.3 micron are considered small MLV and those having size distribution of greater than 0.5 micron are considered large MLV.

"LUV" means large unilamellar single lipid bilayer vesicles having average diameters greater than 0.5 micron.

"REV" means oligolamellar or unilamellar liposomes formed by the reverse phase evaporation method.

"SUV" means small unilamellar liposomes having average size less than 0.1 micron.

"CT" means calcitonin, a peptide hormone which regulates calcium levels in blood and bone regeneration in various species.

"sCT" means salmon calcitonin which is a calcitonin having the same amino acid sequence as calcitonin extracted from salmon.

Preparinq the Liposome Compositions

A. Lipid Components

The liposomes are formed from standard vesicle-forming lipids, which generally include neutral and negatively charged phospholipids with or without a sterol, such as cholesterol. The selection of lipids is generally guided by considerations of (a) desired liposome size and ease of liposome sizing, and (b) lipid and water soluble drug release rates from the site of liposome injection.

Typically, the major phospholipid (PL) components in the liposomes are phosphatidylcholine (PC), phosphatidylglycerol (PG), phosphatidylserine (PS), phosphatidylinositol (PI) or egg yolk lecithin (EYL). PC, PG, PS and PI having a variety of acyl chain groups or varying chain length and degree of saturation are commercially available, or may be isolated or synthesized by well-known techniques. In general, less saturated PLs are more easily extruded, particularly when the liposomes must be sized below about 0.3 microns, for purposes of filter sterilization or other formulation requirement. Methods used in sizing and filter-sterilizing liposomes are discussed below.

The acyl chain composition of the phospholipids may also affect the rate of clearance of liposome lipids and entrapped compound from the site injection, although acyl-chain saturation effects appear to have less of an effect on drug release rates than when liposomes are administered intravenously. Preferred PC and PG are egg (EPC) or soy PC (SPC) or egg PG (EPG), both being derived from either egg or soy phospholipids, and containing a mixture of both saturated and unsaturated acyl chain groups. These are also available in varying extent of hydrogenation.

Experiments conducted in support of the present invention, and reported in Examples IV and VII below, show that negatively charged phospholipids significantly increase the rate of clearance of lipid and entrapped compound from the site of an IM injection, when compared with liposomes formed from PC alone or PC/cholesterol mixtures. Although the studies involved liposomes formulated with selected mole ratios of PG, all other negatively charged phospholipids could be used. The PG effect observed appears to be related, in part, to the ability of charged lipids to prevent spontaneous liposome aggregation in vitro and in vivo. Size measurements on liposomes after extrusion through a 1 micron pore size polycarbonate membrane, reported in example IV, show that PG containing liposomes have stable sizes of about 1 micron, whereas liposomes containing only PC have particle sizes between about 3-5 microns. As will be seen below, and according to one important feature of the method of the invention, larger liposome sizes show longer drug release times at an IM site of injection.

Evidence presented in Examples III and VII indicate that negatively charged phospholipids may also increase in situ lipid and drug release by a mechanism unrelated to liposome size. Briefly, liposomes composed of pure PG (plus a small amount of alphatocopherol) showed more rapid clearance of lipid tracer and a radiolabeled encapsulated drug than similar-sized liposomes containing only 5 or 10 mole percent PG.

The effect of added cholesterol on drug and lipid release from an IM site of injection was also examined. In general cholesterol is known to increase liposome stability, and therefore might be expected to increase the time required for clearance of lipid and entrapped components from an IM site. As reported in Example V, liposomes containing PC and cholesterol, in a mole ratio of about 6:4, showed approximately 20% longer release time of encapsulated peptide than pure PC liposomes. However, addition of cholesterol to PG-containing liposomes produced very little change in the rate of release of either lipid or encapsulated peptide from the site of injection.

B. Protective Aqents

It is well known that the lipid components of liposomes promote peroxidative and free radical reactions which cause progressive degradation of the liposomes. This problem has been discussed at length in the above-mentioned U.S. Pat. No. 4,797,285. Briefly, the patent reports that lipid peroxidative and free radical damage effect both lipid and entrapped drug components in a liposome/drug composition. The extent of free radical damage to lipid and drug components was reduced significantly when a lipophilic free radical quencher, such as alpha-tocopherol (a-T) was included in the vesicle-forming lipids. Interestingly, a significantly greater reduction in lipid damage and drug modification was observed when the liposome/drug composition was formulated in the presence of both a-T and a water-soluble, iron-specific chelator, such as ferrioxamine. Since ferrioxamine can complex tightly to ferric iron at six coordination sites, it is likely that the compound act by inhibiting iron-catalyzed peroxidation in the aqueous phase of the liposome suspension. The effectiveness of the two protective agents together suggests that both iron-catalyzed peroxidative reactions occurring in the aqueous phase, and free radical reactions being propagated in the lipid phase are important contributors to lipid peroxidative damage.

The lipophilic free radical scavenger used in the composition is preferably a-T, or a pharmacologically acceptable analog or ester thereof, such as alpha-tocopherol succinate. Other suitable free radical scavengers include butylated hydroxytoluene (BHT), propyl gallate, and their pharmacologically acceptable salts and analogs. Additional lipophilic free radical quenchers which are acceptable for parenteral administration in humans, at an effective level in liposomes, may also be used. The free radical quencher is typically included in the lipid components used in preparing the liposomes, according to conventional procedures. Preferred concentrations of the protective compound are between about 0.2 and 2 mole percent of the total lipid components making up the liposomes; however, higher levels of the compound, particularly a-T or its succinate analog, are compatible with liposome stability and are pharmacologically acceptable.

The water soluble iron-specific chelating agent is selected from the class of natural and synthetic trihydroxamic acids and characterized by a very high binding constant for ferric iron (in the order of ) and a relatively low binding constant for 2-valence cations, such as calcium and magnesium. A variety of trihydroxamic acids of natural origin are known and available, including compounds in the ferrichrome class, such as ferrichrome, ferrichrome A, and albomycin: compounds in the ferrioxamine class, including the ferrioxamines and ferriomycines; and compounds in the fusaramine class.

One preferred chelator is ferrioxamine B, also known as ferrioxamine, desferrioxamine, desferrioxamine B, and Desferral TM. This compound shows exceptional iron binding affinity and has been proven safe for parenteral use in humans in treating iron-storage disease and iron-poisoning.

The chelating agent is present in the composition at a concentration which is in molar excess of the ferric iron in the liposome suspension. Typically, aqueous media used in liposome preparation contains at least about 1-2 uM ferric iron, and may contain up to 100 uM or more ferric iron. For aqueous medium containing up to about 20 uM iron, concentrations of chelating agent of about 50 uM are preferred.

The chelating agent is preferably added to vesicle-forming lipids at the time of liposome formation, so that the lipids are protected against drug-promoted lipid oxidation damage during liposome preparation. Methods for preparing liposomes by addition of an aqueous solution of chelating agent are described below. Here it is noted only that the liposome suspension formed by this method contains chelating agent both in the bulk aqueous phase and in encapsulated form, i.e., within the aqueous internal liposome region. Alternatively the chelating agent may be included in the suspension after liposome formation.

C. Entrapoed Comoound

The compounds entrapped in the liposomes are a liposome impermeable and/or water soluble drugs such as peptides, antibiotics, hormones and other drugs whose rate of diffusion out of liposomes is not significantly greater than the rate of breakdown of liposomes at an IM site of injection. The encapsulated drug may be a lipophilic drug or hormone whose oil/water partitioning strongly favors the liposome bilayer phase, or a water-soluble drug or peptide which is capable of diffusing across the liposomal bilayer slowly, if at all. Specifically excluded from the invention are all lipophilic or water-soluble drugs which can freely diffuse out of liposomes with a half-life of less than two hours.

Peptide hormones and immunological activators are one important class of compounds for use in the invention. Representative peptide hormones include insulin, growth hormone, EGF and calcitonin, which regulates calcium blood levels. Interferon and interleukin-2 are representative of immunological activators. Gentamicin and amikacin are representative of antibiotics. The present invention allows the selected compound to be released into the bloodstream at a slow, controlled rate over a several hours to several days period, thus avoiding the large fluctuations in drug blood levels that are characteristic of free drug administration.

In addition, and in accordance with one of the discoveries of the present invention, liposomes may significantly enhance the stability of the peptide on storage, when the peptide is present at a relatively low concentration. Stability studies are reported in Example II and summarized in Table 2. These studies show that at 4° C. free drug present at low concentration in the presence of carrier protein, bovine serum albumin, of 0.01 mg/ml for a period of 28 days loses substantially its biological activity. Free drug present in about 100 times more amount (1.0 mg/ml) preserves its activity, i.e., is stable for 128 days. The same small amount 0.01 mg/ml of drug encapsulated in liposomes not only does not lose its biological activity, but preserves the biological activity of the drug for at least 215 days or more. Similarly, at room temperature, both free drug in large amount and liposomal drug in small amounts are stable for 43 days preserving their biological activities. At 98 days both of these formulations show some decrease of activity but still more than 60% of activity is maintained. At 37° C. the large concentration of free drug's biological activity is only about 60% at day 7, while theliposomal form in low concentration is still around 75%. Thus, the invention allows water soluble drugs such as peptides, hormones, antibiotics, anti-tumor agents, and other drugs which are more stable at high concentrations to be stored and delivered in a relatively dilute form in which the high-concentration microenvironment of the drug promotes good stability on storage. The preparation of liposomes which encapsulate water-soluble drugs, such as CT and gentamicin, at a selected internal volume concentration are considered below.

Steroid hormones and anti-inflammatory agents are another important class of compounds which are useful in the present invention. Representative steroids include hydrocortisone, cortisol, estrogens, androgens, estradiol, and testosterone. Liposomes containing entrapped steroids are readily formulated by including the compounds in vesicle-forming lipids. The rate of release of the steroids from the site of IM or SQ injections is be controlled by the partition coefficient of the drug, as well as by liposome stability in and migration from the site of injection.

Other types of compounds which are suitable for slow release liposome delivery from an IM or SQ site include antibiotics, immunosuppressives, such as cyclosporin, and anti-tumor agents, such as doxorubicin.

D. Lioosome Preparation

A variety of methods available for preparing both empty and drug containing liposomes, have been reviewed by Szoka (1980) and include methods such as thin-film hydration, reverse phase evaporation vesicles (REVs) described in (U.S. Pat. No. 4,235,871, U.S. Pat. No. 4,241,046), solvent injection (U.S. Pat. No. 4,752,425 and U.S. Pat. No. 4,718,871), freeze drying, dehydration/rehydration, preparation of stable plurilamellar large liposomes (U.S. Pat. No. 4,522,803), preparation of liposomes in a monophase (U.S. Pat. No. 4,588,578) and liposome extrusion method (U.S. Pat. No. 4,737,323) are all applicable and the patents cited above are hereby incorporated by reference. One preferred method produces multilamellar vesicles (MLVs) of heterogeneous sizes. In this method, vesicle-forming lipids, including a lipophilic free radical protecting agent, and if suitable, a lipophilic drug compound, are dissolved in a suitable organic solvent or solvent system and the solvent(s) are removed under vacuum or an inert gas to form a dry thin lipid film. If desired, the film may be redissolved in a suitable solvent, such as tertiary butanol, and then lyophilized to form a more readily hydrated powder of homogeneous lipid mixture. This film is covered with an aqueous medium and allowed to hydrate, typically over a 15-60 minute period with agitation. The size distribution of the resulting MLVs can be made to have smaller sizes by hydrating the lipids under more vigorous agitation conditions.

The preferred method for instant and spontaneous formation of homogeneous preparation of large liposomes and empty liposomes is adding the water or aqueous solvent to the dry phospholipid film deposited on a specially prepared surface, such as for example etched silicon wafers of which the topography forms a template determining the size of LUVs. The surface of the template determines the size of the formed LUVs. The formation of multilamellar vesicles is prevented by the use of charged phospholipids or neutral phospholipids which are slightly doped, from 1 to 5 wt%, or possibly more, with charged phospholipid(s) or other charged surfactant. The combination of both above assures almost homogeneous size population of LUVs.

Neutral phospholipids, such as PC are charged by spiking or doping with small amount of any other charged phospholipid or of detergent, such as anionic or cationic detergent, examples being sodium dodecylsulfate, oleic acid, soaps or preferably cationic detergent, examples being sodium dodecylsulfate, oleic acid, soaps or preferably cationic detergent cetyltrimethylammonium bromide (CTAB). The mixture of PC and the detergent is dissolved and mixed in an organic solvent, such as halogenated hydrocarbons and aliphatic alcohols, preferably in a mixture of trichloromethane/methanol in amounts from 0.1 to 3 mg of PL, with from 0.5 to 10 wt% of the detergent and 1–10 ml of organic solvent mixture, preferably in amounts 0.5–1 mg of PL, 1.5–5 wt% of the detergent, and 3 ml of the solvent mixture. For charged PL, it is not necessary to use any detergent and these PLs are directly mixed with the solvent in the same amount range.

The above obtained mixture is deposited on the support template surface. The template can be any natural or artificially made rough surface material such as ceramic or nonceramic microfilters, diffraction grids, CD recorded disks, turn table records, sanding paper and such others, made of polyethylene, plastics, ceramics, silicon, metals, glass, wood, fibers and such others, made or manufactured by method such as cutting, sanding, etching, sputtering or any other method suitable and available to make such templated surfaces. Preferably, the support template surface is an etched silicon wafer.

Micropattern for preparation of support template surface that would enable formation of large uniform vesicles consists of small areas of regular shape, such as indentions, pores, holes, etc., which are repeated at a uniform distance across the entire substrate. Micropattern form the matrix for sizing LUVs.

The dimensions of the regular shape are as small as possible. For instance the pattern can be (a) square chess board pattern; (b) rectangular stripe pattern; or (c) isolate regular shapes.

The phospholipid mixture, deposited on the rough support template surface, is dried into a phospholipid film by any means generally used in the laboratory and suitable for drying aqueous and organic solvents, such as for example, drying in a rotary evaporator, under nitrogen flow or in vacuum and followed by high vacuum evacuation. The preferred methods for drying are those where there is a slow evaporation at reduced pressure with no shaking, rotating, or other mechanical disturbance so that the lipid film deposits evenly, at mild temperature from 10°–40° C., preferably at 20 –24° C., at pressures from 300–800 mm Hg, preferably at around 600 mm Hg. The alternative method for the application of phospholipid mixture on the silicon wafer with a template surface is by spinning of the wafer on the spinner similar or identical to the others which are used for applying of the photoresistant in the semiconductor industry. The spinning parameters such as spinning speed between 300–3,000, preferably 1,000 rpm, and spinning time between 0.5 to 20 minutes, preferably three minutes, precisely determine the thickness of the phospholipid film. The above method gives a very uniform film and traces of the remaining solvent can be removed by vacuum drying.

After the solvent evaporation, the deposited phospholipid film is dried for 5–48 hours, preferably overnight under a vacuum, preferably at vacuum of about from $10^{-4}$ to $10^{-3}$ mm Hg.

To form liposomes as LUVs of above 0.5–1 micron size, 0.5–10 ml, preferably 1–5 ml of aqueous medium with or without dissolved drug or other compound to be encapsulated in LUVs, is added to the deposited lipid film on the template surface. By this simple act of water addition, the LUVs of uniform size are formed instantly without use of any mechanical procedure. Thus, no shaking, filtering, sonication, extruding, evaporating, column separation, dialysis, lyophilizing, using absorbers, emulsifying or other intrusive procedures are necessary for liposome formation and for drug encapsulation in LUVs.

The aqueous medium for empty liposomes is typically a buffered aqueous solution having a pH between about 6.0 and 7.5.

The size of the vesicles (LUVs) formed by the process of this invention depends on and is determined by the size of indentions, pores, holes, openings, etc. on the template surface and on its surface topography and is typically larger than 0.5 u.

In forming liposomes with an encapsulated water-soluble compound, such as a peptide hormone, the compound is dissolved in the hydration medium at concentration which is desired in the interior of the liposomes in the final liposome suspension. Thus, for example, to form liposomes encapsulating CT at an interior space concentration of about 1 mg/ml, the hydration medium would contain 1 mg/ml CT. After free drug removal, the drug containing liposomes may be resuspended to a much lower or higher final drug concentration. The hydration medium may also be prepared to include an iron-specific chelator, at a preferred concentration of between about 10–50 mM. Example I describes the specific method of preparation and some of the lipid compositions used in liposome formulations described in subsequent examples. The study reported in Example II shows that the stability of CT in free solutions form is enhanced several-fold when the CT concentration is raised from 0.010 to 1.0 mg/ml. CT which is encapsulated in liposomes at a relatively high concentration— e.g., 1 mg/ml—but present at a relatively low bulk phase concentration—e.g., 0.010 mg/ml — shows the same stability effect seen at high concentrations of the free hormone method of producing a suspension of MLVs encapsulating CT.

Another advantageous method of producing liposomes is the reverse-phase evaporation method described by Szoka (1978). There, a solution of vesicle-forming lipids in an organic solvent or solvent mixture is added to an aqueous solution of the material to be encapsulated, at relative volume amounts which are compatible with a water-in-oil emulsion. The mixture is then emulsified, and the organic phase removed to produce a reverse-phase lipid gel composed of lipid monolayer structures encapsulating aqueous droplets. This gel, when resuspended in an aqueous solution, forms a suspension of relatively large oligolamellar vesicles, commonly referred to as reverse-evaporation vesicles (REVs). The method produces high encapsulation efficiencies, typically between about 30-40% of the total water-soluble material added, and is thus particularly useful for encapsulating expensive drug or peptide compounds, such as peptide hormones.

Regardless of the method used, liposome preparation is preferably carried out under conditions which lead to a sterile liposome suspension. This is accomplished by employing conventional sterile techniques throughout the procedure.

E. Liposome Sizing

Even though initial liposome preparation may be done under sterile conditions, it is generally necessary to treat the preparation to remove free drug, and such treatment generally involves methods which are difficult to carry out aseptically. Therefore, a final sterilization may be required before the liposomes can be used for parenteral injection.

The method of choice for liposome sterilization, and the only method available for sterilizing liposomes containing heat-sensitive encapsulated material, is by filtration through a conventional sterile depth filter, typically a 0.22 micron filter. This method can be carried out on a practical, high through-put basis only if the liposomes have first been sized down to about 0.2-0.3 microns or less.

Several techniques are available for reducing liposomes to this size range. Sonicating a liposome suspension either by bath or probe sonication produces a progressive size reduction down to small unilamellar vesicles (SUVs) less than about 0.05 microns in size. Homogenization is another method which relies on shearing energy to fragment large liposomes into smaller ones. In a typical homogenization procedure, MLVs are recirculated through a standard emulsion homogenizer until selected liposome sizes, typically between about 0.1 and 0.5 microns, are observed. In both methods, the particle size distribution can be monitored by conventional laser-beam particle sizer. Extrusion of liposomes through a small-pore polycarbonate membrane is an effective method for reducing liposome sizes down to a relatively well-defined size distribution (Szoka 1978). Typically the suspension is cycled through the membrane several times until the desired liposome size distribution is achieved. The liposomes may be extruded through successively smaller-pore membranes, to achieve a gradual reduction in liposome size. Preparing large empty liposomes by using template with uniform large size pores, as described in section is also contemplated.

F. Removinq Free Druo

Even under the most efficient encapsulation methods, such as the REV and solvent injection method mentioned above, the maximum encapsulation efficiency for a water-soluble compound is about 50-60%, so that the initial liposome suspension will contain 40% or more of the compound in free (non-entrapped) form. The amount of non-encapsulated material is still higher in a liposome suspension formed by the above MLV method, where encapsulation efficiencies between about 10-20% are typical. The studies reported in Example III show that a free (non-encapsulated) drug is cleared from the site of an IM injection in several minutes, as compared with several hours to several days for liposome encapsulated drug. Therefore, in order to minimize the effect of rapid drug release from the site of injection, it is important to remove free drug which may be present in the newly formed liposome preparation.

Several methods are available for removing non-entrapped compound from a liposome suspension. In one simple method, the liposomes in the suspension are pelleted by high-speed centrifugation, leaving free compound and very small liposomes in the supernatant. The preparation is then resuspended in drug-free buffer and the procedure repeated until the desired low amount of unencapsulated drug level is achieved. Another method of diafiltration involves concentrating the suspension by ultrafiltration, the resuspending the concentrated liposomes in a drug-free replacement medium. Alternatively, gel filtration or size exclusion chromatography can be used to separate larger liposome particles from solute molecules.

Yet another approach for removing free compound utilizes ion-exchange, molecular sieve, or affinity chromatography. Here the liposome suspension is passed through a column containing a resin capable of binding the compound in free, but not entrapped, form, or a support having attached binding molecules, such as antibodies, which bind specifically to the non-encapsulated compound. The approach may also be effective in removing free pyrogens, with proper selection of resin(s).

Following treatment to remove free drug, the liposome suspension is brought to a desired concentration for use in IM or SQ administration. This may involve resuspending the liposomes in a suitable volume of injection medium, where the liposomes have been concentrated, for example by centrifugation or ultrafiltration, or concentrating the suspension, where the drug removal step has increased total suspension volume. Since the free drug removal step is quite involved, it is usually necessary to terminally filter the product through a 0.2 micron sterile filter to guarantee sterility for an injectable product even when the process is performed at low bio-burden.

Liposome Processino

The primary discovery and the main advantages ofthe current invention is illustrated in FIG. 1 is a flow diagram of a liposome processing scheme suitable for preparing theliposome composition of the invention.

The flow scheme at the left in the figure shows steps in forming a sterile suspension of liposomes which have an entrapped compound. The flow scheme at the right of the figure shows step in forming empty liposomes. The steps, necessary in forming liposomes in the encapsulated drug which have been detailed above. Step 1 involves first preparing a suspension of liposomes containing the compound at a selected entrapped concentration. Step 2. The suspension is then sized down to 0.2-0.3 or less, to allow for eventual sterile filtration. Step 3. Removal of non-entrapped drug. Step 4. The material is brought to a desired lipid concentration. Step 5. The formulation is sterilized by filtration. The right hand column in FIG. 1 illustrates parallel steps used in preparing empty liposomes, has only 2 steps when compared to 4 or steps necessary in production of liposome with encapsulated drug.

Step 1 is to prepare a suspension of empty liposomes is followed by Step 2, signing and sterilizing liposomes by filtration which also removes small liposomes.

Thus, provided that the therapeutic effect of the combination of small portion of small liposomes with encapsulated drug and large portion of empty liposomes is similar to or the same, the advantage of this invention is readily understood while the preparation of large volumes of manufactured formulation of small liposomes with encapsulated drug consist of 5 steps, the preparation of the same volume of a mixture of small liposomes with encapsulated drug and large empty liposomes consist of 5 steps for small amount of liposomes and 2 steps for empty liposomes. Thus for example if liters of formulation is needed, by the old process, all 100 liters has to go through 5 steps, while using the procedure of the current invention, only 1 liter needs to go through 5 steps and 99 liter goes through 2 steps only. The savings achieved by the current invention are considerable and highly advantageous to scale up process.

It has been previously shown that the drug encapsulated in large liposomes may have a slower release rate than the one encapsulated in small liposomes. This invention discovered that the same prolonged release can be achieved from the small liposomes with the encapsulated drug if these liposomes are diluted with larger amounts of large liposomes in ratio from 0.1–1 to 10–200 of preferably 1:100 small liposomes to large liposomes.

The resulting mixture having unexpectedlycomparablerelease rate as one having all liposomes encapsulated can be prepared according to FIG. 1 scheme by preparing only small amount of drug encapsulated liposomes by encapsulation of drug in formulation of a sterile liposome suspension, sizing, removing the free drug and sterile filtration. The large amount of empty liposomes, on the other hand can be prepared by forming empty liposome and sterilizing them by filtration sizing. Thus two steps in the process of preparing large drug containing liposomes can be eliminated affording considerable saving of time and material.

The rationale for preparing empty liposomes is based on the discovery herein that the release rate of liposome-encapsulated material from an IM or SQ injection site can be selectively varied by changing (a) thelipid composition, (b) average liposome size, or (c) total lipid amount of the injected liposomes. The relationship between these parameters and compound release rate will be detailed in Section II below, and in Example III–VII. At this point, it is sufficient to note that these effects are achieved even when a large portion of the liposomes injected into the tissue do not contained entrapped compound. That is, the effect oflipid composition, size, and amount on compound release rate appear to depend on liposome-liposome interactions which affect empty and compound-containing liposomes in the same way.

The advantage of empty liposomes, as a method of varying lipid composition, size, and amount, is that they can be prepared readily in sterile form in sizes and need not be terminally sterilized by filtration through a 0.2 micron filter. It will be recalled that the sterility of a liposome preparation may be compromised because of the need for removal of free compound from the suspension. By forming liposomes in the absence of the compound, the final sterile filtration step can be avoided. An important advantage here is that since the empty liposomes do not have to be sized down for filtration, relatively largeliposomes can be added, allowing for greater size-related effects in compoundrelease rate to be achieved. Also, to produce a specified amount of injectable product, the batch size of the drug-containing liposomes and free drug removal process will be at least 10 to 100-fold reduced. Thus, smaller volumes and less of equipment can be used.

Considering the scheme shown at the right in FIG. 1, the empty liposomes may be optionally treated, if desired, to remove smaller liposomes. This can be done, for example, by allowing larger liposomes to settle in a vessel, and aseptically removing non-settled material. Alternatively, the liposomes may be added directly to the filter-sterilized liposomes, without further treatment, to produce a final composition having a selected average lipid composition, size, and concentration, or the liposomes may be sized, such as by extrusion through a 1 micron polycarbonate membrane under sterile conditions, before addition to the filter-sterilized liposomes.

The processing method described above thus allows for the preparation of a sterile liposome formulation having (a) a selected concentration of entrapped compound, (b) little or no free compound, and (c) an average liposome size, concentration and composition which allows the entrapped compound to be released from an injection site to a selected release rate.

Properties of the Composition

A. Stability

One advantageous feature of the present invention is the increased stability of a pharmacological compound, which is achieved with liposome encapsulation. In particular, where the compound is more stable in a concentrated form, such as has been found for CT, liposome encapsulation allows the compound to be stored in stable form in a suspension in which the compound has a high localized concentration, but at relatively low overall concentration. For example, the study reported in Example II shows that free CT is substantially more stable at 1 mg/ml than at 0.01 mg/ml, even in the presence of a carrier protein. When the peptide is encapsulated in liposomes at an internal-volume concentration of 1 mg/ml, but at suspension concentration of 0.01 mg/ml, the peptide shows the stability characteristics of the high concentration of CT.

The stability of the liposomes is enhanced by including a lipophilic free radical quencher, such as a-T, at a mole ratio of at least about 0.2. Further, composition stability may be achieved by addition of an iron-specific chelator, such as ferrioxamine, in molar excess of the amount of free ferric iron in the liposome suspension. The CT/liposomes can be sized, treated to remove free CT, and sterile filtered, as above. The resulting composition includes (a) a sterile, aqueous suspension of liposomes containing at least about 0.2 mole percent a-T, and (b) CT entrapped in the liposomes at a concentration of at least about 1 mg/ml. The concentration of free CT is preferably less than about 10 mole percent of the encapsulated peptide.

The discovery that liposome encapsulation allows a peptide hormone, such as CT, to be stored in stable, dilute form applies to a variety of other peptides and proteins. For example, it would be advantageous to be able to store enzymes in stable, dilute form for a long period of time as over 200 days.

B. Release Characteristics of Lipids and Encapsulated Compound

The clearance rates of lipids and an encapsulated compound from an IM site of injection have been examined, as reported in Examples III–VII. The purpose of the studies was two fold: (1) to determine the relationship between lipid and peptide clearance from an injection site, and (2) to examine the liposome variables that affect peptide release rate. Although the studies were performed using CT as a model peptide compound, it will be recognized that the findings are applicable to any water-soluble compound that would require liposome breakdown for its release into the bloodstream.

Figure 5:
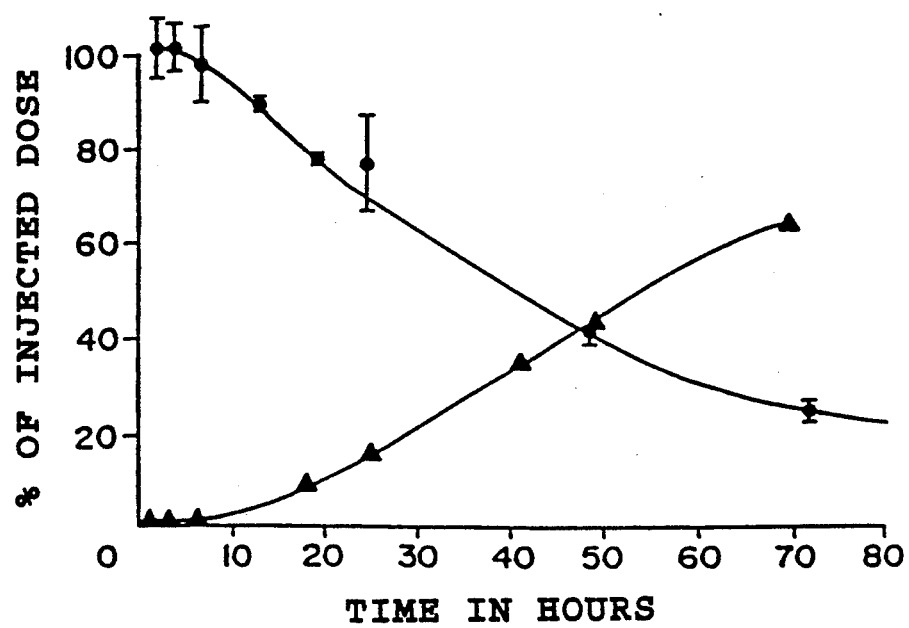
FIG. 5 shows the kinetics of clearance of a radiolabeled lipid component in liposomes from the site of an IM injection (circles) and the accumulation of tracer (triangles) excreted in urine and feces from the injected animal.
Figure 6:
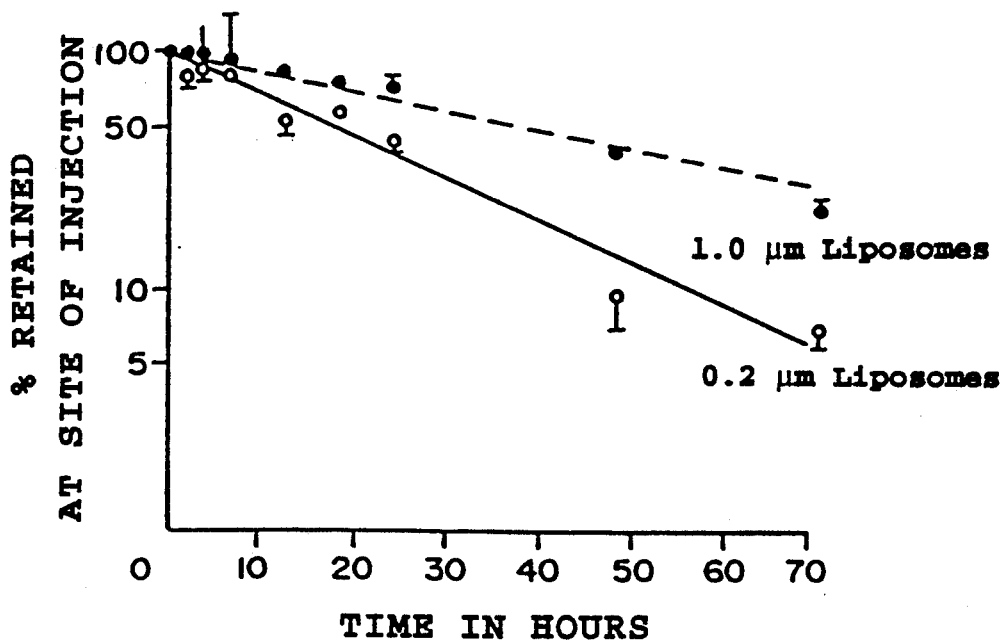
FIG. 6 is a semi-log plot of the radio-labeled lipid release data (dotted line) and analogous tracer release data from liposome composition with smaller liposome sizes (solid line).

To follow the rate of clearance of liposome lipids from an IM injection site, liposomes containing $^{125}$I-labeled phosphatidylethanolamine ($^{125}$I-BPE) as a tracer lipid were injected into the limbs of laboratory animals. The disposition of the tracer lipid was measured at a minimum of eight time points over at least a 70-hour test period. The loss of tracer from the sites of injection (circles) and accumulation of the excreted tracer (triangles) are seen in FIG. 5. The data on tracer clearance from the site of injection, when plotted as a semi-log function, gives a linear plot, such as seen in FIG. 6, from which the lipid clearance half life can be calculated. Details of the method are given in Example VII.

Figure 2:
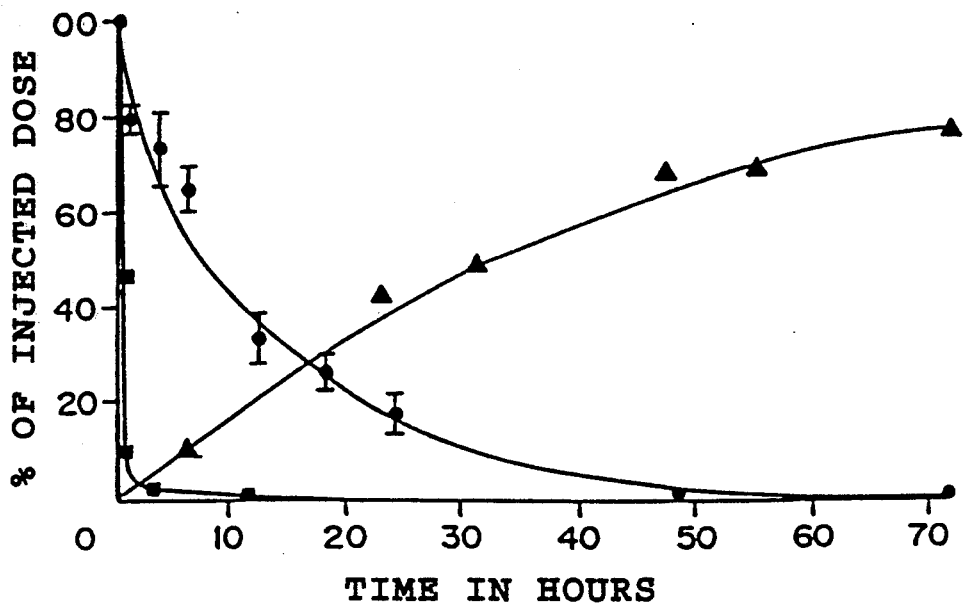
FIG. 2 shows the kinetics of release of liposome encapsulated radioactive calcitonin (CT) from the site of an IM injection (circles), the cummulative excretion of radio-activity of hormone (triangles) from the animal, and release of free CT from the site of injection (squares).

The clearance of $^{125}$I-radiolabeled CT from liposomes injected intramuscularly in animals was followed. FIG. 2 shows plots of the loss of tracer from the sites of injection (circles) and accumulation of excreted tracer (triangles) from a typical experiment. A semi-log plot of the CT clearance, shown in FIG. 3, was used to calculate clearance half-life from the site of injection. The linear relationship between the log of retained CT and time indicates that lipid is cleared from the site of injection with first order kinetics. Also shown in the figure is the rapid clearance of free CT from the sites of injection into the boodstream. Example V shows that IM and SQ administered CT liposomes have comparable clearance rates for the formulations.

The effect of liposome size on lipid and CT clearance rates is apparent form the data in Example IV comparing liposomes with sizes ranging from 0.2 microns to about 5 microns, with larger liposomes showing 60–100-% longerlipid clearance rates. The data in Example VII show that the clearance of half-life of lipid tracer from small liposomes (about 0.2 microns) can be increased by addition to the injected liposomes of larger unlabeled liposomes (about 1 micron). The latter results indicate that lipid clearance is governed by bulk effects related to average liposome sizes, and forms the basis, according to one aspect of the invention, of controlling release characteristics of smaller liposomes by the addition of larger, empty ones.

The effect of liposome dose on lipid clearance is also reported in Example IV. As discussed therein, lipid clearance half life can be increased more than twofold with increased lipid dose, independent of lipid size or composition. The same two-fold increase in clearance rate with increased dose is seen for encapsulated CT (Example V). Interestingly, a comparison of lipid and CT release rates from liposomes having the same size and dose properties (Example V), shows that CT clearance from the site of injection is about twice as fast as that of the corresponding lipid tracer. This finding suggests that liposomes are destabilized and release their encapsulated contents predominantly at the site of injection, with lipid clearance from the site being handled by a different, slower mechanism.

The effect of lipid composition on lipid and CT clearance from an IM site was also examined. As discussed above, and reported in Examples IV and V, addition to the liposomes of a negatively charged phospholipid, such as PG, significantly increases the rate of clearance oflipid and encapsulated CT from an IM site. As noted in Example IV, the PG effect may be related in part to the reduced liposome aggregation which is seen in PG-containing liposomes.

Cholesterol, at a mole ratio of about 40%, hadlittle effect on lipid clearance from PG-containing liposomes, but showed a slgnificant stabilizing effect—that is, longer clearance half llfe—on CT release from neutral, PC liposomes. CT was cleared about twice as rapidly as lipid tracer from liposomes having the same size and lipid composition properties, confirming that liposome lipid is cleared from the injection site by a different, slower mechanism than that acting on the encapsulated compound.

The results above show that release of an encapsulated cumpound from liposomes at an injection site can be controlled selectively by changes in liposome size, dose, and lipid composition, specifically, in practicing the method of the invention, the rate of release of an encapsulated compound from an injection site is controlled according to an average size and total amount of liposome injected into the site. In one aspect of the invention, average size and lipid amount are selectively increased by adding larger, empty liposomes to smaller, filter sterilized liposome encapsulating the compound of interest.

Greater release time can also be achieved, according to the invention, by adding cholesterol to either or both of the compound-containing or empty liposomes. To achieve faster release of the encapsulated compound, the liposomes can be formulated to include progressively more negatively charged lipid, such as PG.

Therapeutic Uses

The liposome composition of the invention is useful for administering a variety of liposome-impermeable compounds parenterally preferably intramuscularly or subcutaneously. One important application is for use in administering a peptide hormone or immunomodulator to bloodstream in a controlled fashion over a several day period. The composition allows the halflife of peptide release to be selectively varied, to provide release for a selected period of up to several days. The peptide can then be given less often and without the sharp fluctuations seen when free peptide injections are used. Further, a greater degree of control can be achieved than with liposome formulations which have been proposed heretofore.

Insulin and CT are examples of peptides which are now routinely administered in free form. Both of these peptides are readily incorporated into the liposome composition of the invention, and both can be delivered over a several day period by IM injection the composition. The rate of hormone delivery is controlled, according to the method of the invention, by use of selected average liposome size, amount, and composition. For some peptides, such as CT. an added benefit of the liposome composition is the increased stability which is achieved, allowing the material to be stored in relatively dilute form over an extended period.

The following examples describe particular embodiments of making and using the invention, but are in no way intended to limit the invention.

EXAMPLE I

Preparation of sCT/MLVs

Egg phosphatidylcholine and egg phosphatidylglycerol were supplied by Avanti Lipid (Birmingham, AL). The lipids were judged about 99% pure by thin-layer chromatography. Cholesterol (CH) and alPha-tocopherol (a-T) were obtained from NuChek Prep. Inc., (Eysian, MN) and Sigma Chemical Co., (St. Louis, MO), respectively, both at a purity of about 99% or greater. Salmon calcitonin (sCT) was $^{125}$I-radiolabeled with 125I by the chloramine T method (McFarland).

Multilamellar vesicles (MLVs) containing one of the lipid compositions A-E indicated in Table 1 were prepared. The molar ratios of the lipid components in the five vesicle preparations are shown in Table 1. The values in the table indicate the molar ratios of each lipid component that were used in forming the various vesicle preparations. For studies to measure the rate of clearance of liposome lipid from an intramuscular site of injection, the vehicle-forming lipids also included a radioactive iodinated derivative of hydroxybenzamidine phosphatidylethanolamine ($^{125}$I-BPE) tracer. To form the tracer, the p-hydroxybenzamidine of egg phusphastidylethanolamine (BPE) was synthesized as described by Abra et al., (1982a) and this compound was iodinated with $^{125}$I, as described by Greenwood. The specific activity of the stock was $3.85 \times 10^6$ cpm per nmole PE. The iodinated lipid was incorporated at $1 \times 10^5$ cpm per injection in the range of 0.2 to 10 umole total lipid.

TABLE 1

| Composition | Molar Ratios | | | |
|---|---|---|---|---|
| | EPC | EPG | CH | a-T |
| A | 99 | — | — | 1 |
| B | 94 | 5 | — | 1 |
| C | 49 | 5 | 40 | 1 |
| D | — | 99 | — | 1 |
| E | 59 | — | 40 | 1 |

To form MLVs, the lipid components in chloroform stock solution were mixed in a tube or round bottom flask. The chloroform was removed by rota-evaporation and the lipid mixture was dissolved in appropriate volume of t-butanol to completely solubilize the lipid mixture. The butanol solution was then frozen in dry-ice/acetone and lyophilized overnight. The dry lipids were hydrated in phosphate buffered saline (PBS), pH 7.4. For the studies involving CT/MLVs, the hydration buffer contained 0.2-5 mg/ml of sCT sPiked with $^{125}$I-sCT to estimate percent encapsulation.

The lipid film was hydrated with vortexing for about 15 minutes at room temperature to form an MLV suspension having heterogeneous sizes ranging from about 0.2 to 10 microns. The vesicle preparations were sized by extrusion through a polycarbonate membrane having selected pore sizes. The entire preparation was extruded through a 1.0 micron polycarbonate membrane, producing vesicles which had an initial vesicle size (before any aggregation in case of neutral liposomes) of about 1 micron. In forming smaller-size vesicles, the sized vesicles were further extruded successively through 0.4 and 0.2 micron pore size membranes, to produce vesicles with sizes in the 0.2 micron size range.

MLVs containing encapsulated sCT were freed of non-liposome-associated free sCT by washing three times in PBS by centrifugation. The formulations were tested for pyrogens by the Limulus Amoebic Lysate assay (Haemachem., Inc., St. Louis, Mo). Preparations which showed negative in this test were used in the animal experiments.

EXAMPLE II

Stability of Liposome Encapsulated sCT

Composition B MLVs containing 1.0 mg/ml encapsulated sCT were prepared as in Example I. The liposomes were extruded successively through 1.0 and 0.4 polycarbonate filters and washed three times in PBS to remove free sCT. The liposomes were diluted tu final concentration of 0.010 mg/ml sCT, and sterilized by passage through a standard sterile 0.45 um Acrodisc filter, and aliquoted into sterile Nunc vials. Sterilized solutions of free sCT containing either 0.010 or 1.0 mg/ml in PBS with 0.5% BSA as carrier were also aliquoted into the vials. The liposome-encapsulated and free sCT preparations are referred to in Table II as L-sCT and F-sCT, respectively.

The stability of the F-sCT and L-sCT preparations as indicated by the sCT hypocalcemic activity were tested after incubating the samples at either 4° C., room temperature (about 24° C.) or 37° C. The liposomes samples were lysed in 0.1% triton-X 100 (obtained from Sigma Chemical Co., St. Louis, MO) and diluted to approximately 40 and 120 mU per ml in PBS/BSA. (One microgram of sCT has 4,000 mU of activity.) F-sCT stability samples were treated slmilarly. The biological activity of these samples were compared wlth those of a frozen standard solution diluted in PBS/BSA prior to the bioassay in the range of 12 to 120 mU/ml.

Fasted rats (four rats per group) were injected subcutaneously with 0.25 ml of either the diluted test samples or the standard solutions. Control rats received only PBS/BSA. At exactly sixty minutes after injection, blood samples were drawn from each rat. The blood samples were allowed to clot and serum samples were collected by centrifugation. The calcium levels in the sera were determined by the colorimetric assay supplied by Sigma Chemical Cu. (procedure no. 586). Absorbance due to hemolysis was corrected by subtracting the absorbance at 575 nm of the serum sample diluted in water instead of the reagent. The hypocalcemic activity of the samples were determined from the standard curve constructed from the rats which had received the standard sCT. Typically, the standard curve consisted of four points: 0, 3, 9 and 27 mU or 0, 5, 10 and 30 mU per rat. The results were plotted in semi-log paper and the hypocalcemic effect of the test samples were expressed as mU of activity. The activity of the stability samples in Table 2 were expressed as a percentage of the respective samples at the beginning of the storage period.

TABLE 2

| No. | Sample | [sCT] (mg/ml) | Temp. (°C.) | Time (days) | Activity (%) |
|---|---|---|---|---|---|
| 1 | F-sCT | 0.01 | 4 | 128 | 27 |
| 2 | F-sCT | 1.0 | 4 | 128 | 100 |
| 3 | L-sCT | 0.01 | 4 | 128 | 100 |
| 4 | L-sCT | 0.01 | 4 | 215 | 100 |
| 5 | F-sCT | 0.01 | RT | 43 | 40 |
| 6 | F-sCT | 1.0 | RT | 43 | 100 |

TABLE 2-continued

| No. | Sample | [sCT] (mg/ml) | Temp. (°C.) | Time (days) | Activity (%) |
|---|---|---|---|---|---|
| 7 | L-sCT | 0.01 | RT | 43 | 100 |
| 8 | F-sCT | 1.0 | RT | 98 | 61 |
| 9 | L-sCT | 0.01 | RT | 98 | 62 |
| 10 | F-sCT | 1.0 | 37 | 7 | 62 |
| 11 | L-sCT | 0.01 | 37 | 7 | 74 |

The first three rows compare the stability of dilute and cuncentrated solutions of F-sCT and a dilute solution of L-sCT over a 128-day period at 4° C. As seen, dilute F-sCT, but not L-sCT, ses most of its activity during this period. The liposome stabilizing effect is presumably due to the locally high cuncentration of sCT (about 1 mg/ml) within the liposome aqueous space. As seen in row 4, encapsulated sCT in a dilute solution is able for at least 215 days.

A similar liposome-protective effect is seen with sCT incubated at room temperature. Over a 43-day incubation period, a dilute solution of F-sCT has lost about 60% of its activity, but the concentrated F-sCT and dilute L-sCT preparations showed no activity luss. That the latter two preparations have about the same stability is seen from the data for 98-day incubation at room temperature, and that for 7-day incubation at 37° C.

The study reported in Example II thus shows that the sIability of CT in free form is enhanced several-fold when the CT concentration is raised from 0.010 to 1.0 mg/ml. CT which is encapsulated in liposomes at a relatively high concentration e.g., mg/ml—but present at a relatively low bulk phase concentration—e.g., 0.010 mg/ml—shows the same stability etfect seen at high concentrations of the free hormone.

EXAMPLE III sCT Clearance from the Site of an Intramuscular Injection

The rate of clearance of sCT from a given liposome furmulation was determined by monitoring the clearance of $^{125}$I-sCT from the intramuscular site of injection. Salmon calcitonin was spiked with $^{125}$I-sCT and encapsulated in MLVs as described in Example I in such a way that after the removal of non-liposome associated drug, the injection sample contained about 10,000 cpm of $^{125}$I per injection. It should be noted that the radiolabeled sCT has comparable hypocalcemic activity to the original sCT before iodination with $^{125}$I.

Figure 3:
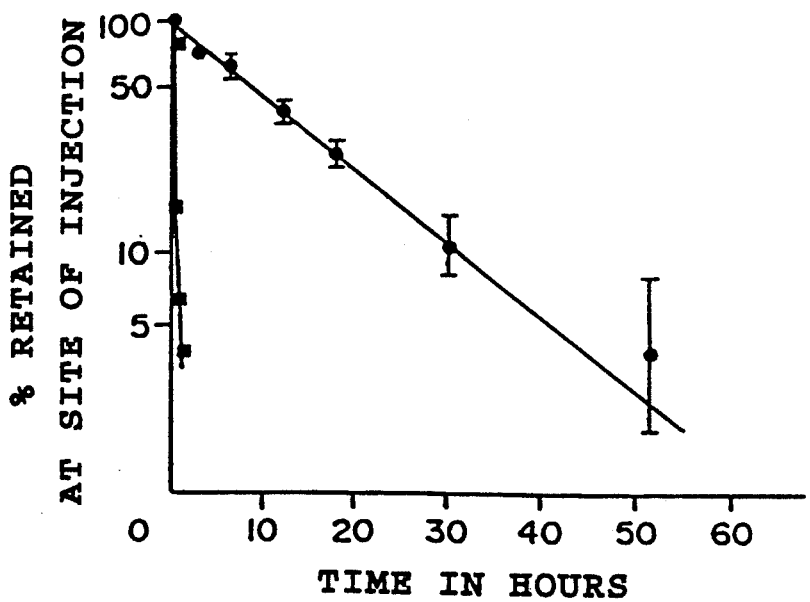
FIG. 3 is a semi-log plot of CT release data from FIG. 2.

Male Sprague-Dawley rats weighing 95 to 100 g were lightly anesthetized with ether, and 20 ul or 100 ul of the $^{125}$I-sCT liposome samples were injected either in the lower part of the forelimbs or the hindlimbs respectively. Sixteen to twenty rats were used in each experiment. In experiments in which the fate and distribution of the radiolabel was followed, two of the rats were placed in metabolic cages to monitor the excretion of the radiolabel in the urine and feces. At least eight time points were taken for each experiment over a test period of three to six days. At each time point, two rats were anesthetized for blood sampling (two ml blood were drawn and counted for $^{125}$I radioactivity). The rats were then killed by asphyxiation in a $CO_2$ chamber. Each of the injected limbs was dissected at the knee joint taking care not to disturb the injected sample. The limbs were inserted into tubes and then counted for remaining radioactivity in a gamma counter. The eight to ten time points shown in FIG. 2 were selected so that the half-life of clearance from the IM site could be determined by a semi-log plot of the radioactivity remaining versus time after injection as shown in FIG. 3. For comparison, the clearance of free $^{125}$I-sCT from the injection site was shown in FIG. 2 also. IT was apparent in FIG. 2 that the free drug cleared extremely rapidly.

The urine and feces from the two rats kept in metabolic cages throughout the experiment were collected and counted for radioactivity. At the last time point, the animals were sacrificed as described above and were also dissected for their thyroid glands, lungs, heart, liver, spleen, stomach, intestines and genitals for counting. The carcass was digested prior to counting. Radioactivity levels were measured to determine the disposition of residual $^{125}$I in the animals at the end of the experimental period.

The results of a typical experiment are shown in FIG. 2. Free sCT cleared from the site of injection extremely rapidly as shown in the square points. In the liposome formulation, the radiolabeled drug cleared much more slowly (closed circles). The error bars indicate the spread between two animals (i.e. total 4 limbs) at each time point. The cumulative excretion of the radiolabel from liposome formulation in the urine and feces increased steadily throughout the experiment. The semi-log plots of the percent radiolabeled drug at the site of injection from liposome furmulation and free drug were shown in FIG. 3. The clearance half-life was determined from the plots and in this experiment, the free sCT cleared with a half-life of a few minutes while that of the liposome formulation shown was about 9 hours. In a typical experiment, at the last time point where greater than 90% of the injected radio-label had cleared from the injection site, most of the radiolabel was excreted in the urine (about 80%), and about 5% was excreted in the feces, several percent was in the thyroid gland, several percent was associated in the digested carcass, barely detectable levels were observed in the blood. The total recovery was usually about 95 to 100% of the injected dose.

EXAMPLE IV

Effect of Liposome Dose and Composition on the Clearance of sCT from an IM Injection Site sCT-MLVs were prepared as described in Example I with $^{125}$I-sCT as marker such that about 10,000 cpm was injected as in Example III. The clearance half-lives from the various sCT-MLV formulations were determined as described above. Table 3 summarized the cearance half-lives of several sCT formulations injected in different lipid doses.

TABLE 3

| No. | Composition | Size (micron) Extruded | Size (micron) Measured | Lipid Dose/ Injection (umole/ul) | T ½ (hours) |
|---|---|---|---|---|---|
| 1 | A | 1.0 | 3.2 | 0.2/20 | 48.7 |
| 2 | A | 1.0 | 3.2 | 2/100 | 57.6 |
| 3 | A | 1.0 | 5.4 | 10/100 | 100.7 |
| 4 | B | 0.2 | 0.23 | 0.2/20 | 17.8 |
| 5 | B | 1.0 | 1.3 | 0.2/20 | 33.3 |
| 6 | B | 1.0 | 1.0 | 10/100 | 62.2 |
| 7 | C | 0.2 | 0.25 | 0.2/20 | 15.3 |
| 8 | C | 1.0 | 1.1 | 0.2/20 | 26.8 |
| 9 | C | 1.0 | 1.0 | 10/100 | 69.4 |
| 10 | D | 1.0 | 0.9 | 10/100 | 17.7 |

As shown in the table, increase in the lipid dose of liposome formulations of identical lipid composition prolonged the clearance half-life from the IM injection site and the incorporation of cholesterol also prolonged the clearance half-life. Increasing the size of liposomes also prolonged the clearance half-life of the drug.

EXAMPLE V

Effect of Intramuscular Versus Subcutaneous Route of Administration on the Clearance Half-life of sCT-MLVs The clearance half-lives of three sCT-MLV formulations were determined as described above to compare intramuscular versus subcutaneous routes of injection. The results are summarized in Table 4.

TABLE 4

| sCT-MLV | Route/Site of Administration | Lipid Dose (umole/ul/injection) | T ½ hours |
|---|---|---|---|
| EPC/EPG/a-T | IM/forelimb | 0.2/20 | 9.8 |
|  | SQ/forelimb | 0.2/20 | 7.0 |
| DPPC/DPPG/a-T | IM/forelimb | 0.2/20 | 9.7 |
|  | SQ/forelimb | 0.2/20 | 8.3 |
| EPC/a-T | IM/hindlimb | 0.2/100 | 20.4 |
|  | SQ/hindlimb | 0.2/100 | 19.4 |

As seen in the results, there was no significant difference in the half-lives of clearance by the two routes of administration. Therefore the rate of clearance from either IM or SQ routes of administration were approximately the same.

EXAMPLE VI

Plasma Levels of Immunoreactive sCT

Figure 4:
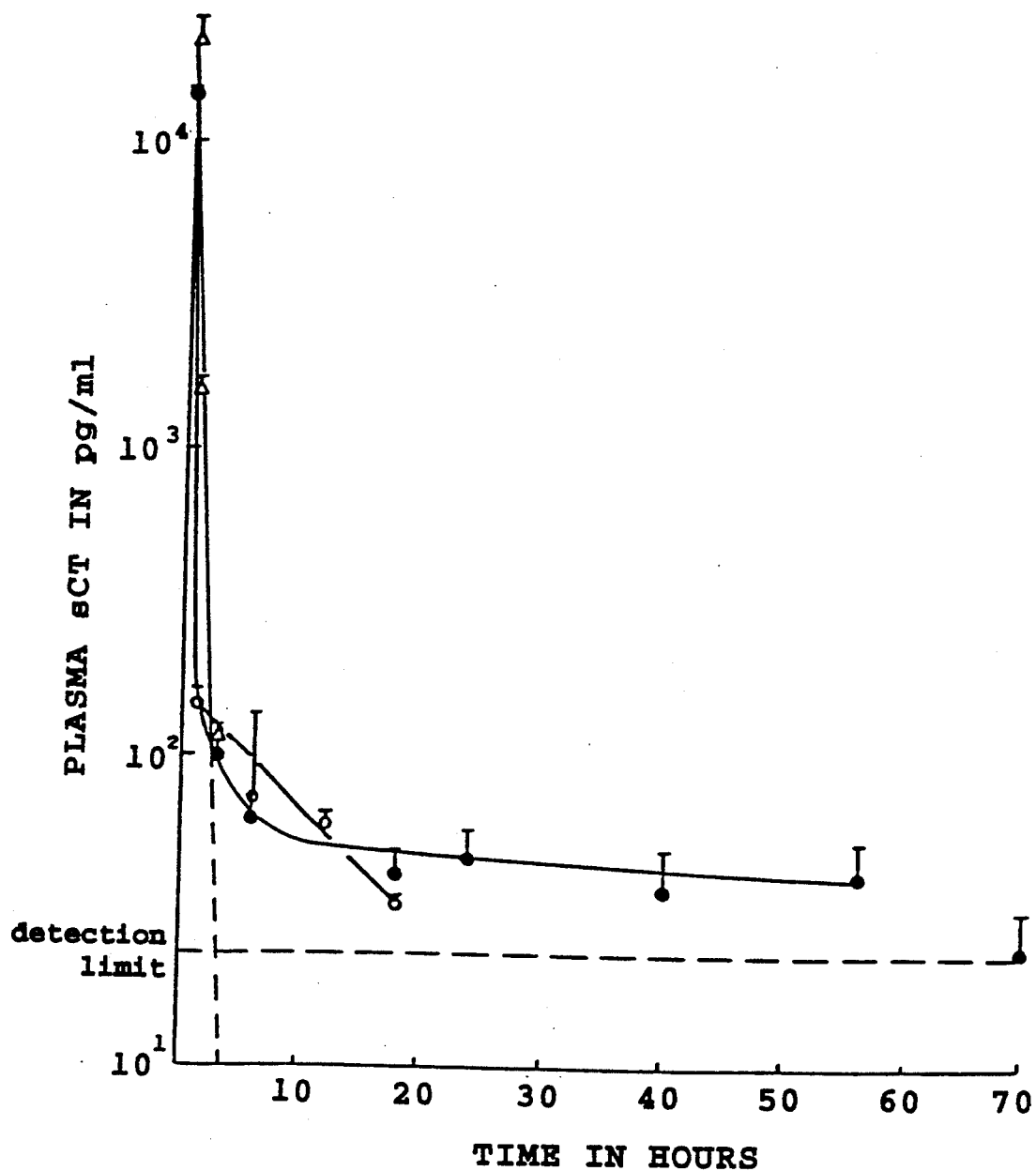
FIG. 4 shows the plasma concentration of immunoreactive salmon calcitonin (sCT) in rats after IM injection of free sCT (triangles), liposomes S-CT(L-sCT) with clearance half-life from injection site of about 10 hours (open circles) and L-sCT with clearance half-life of about 55 hours (closed circles).

Rats weighing 95 to 105 gm were injected intramuscularly in the forelimbs with sCT or sCT-MLVs. At each time point, four rats were bled by cardiac puncture and the blood collected in pre-chilled EDTA containing tubes. The plasma was collected after centrifugation at 4° C. and quickly frozen. The frozen samples were sent to Hazleton Laboratories for sCT radio-immunoassay (RIA). The results are shown in FIG. 4. As seen in the figure, the free sCT (1 ug) (data shown in open triangles) rapidly disappeared from circulation. Rats which had received sCT-MLV formulation (1 ug sCT in 0.35 umole EPC/CH/a-T) with a clearance of half-life of about 10 hours showed detectable blood levels of immuno-reactive sCT up to 18 hours. Rats wnich had received sCT-MLV (21 ug of sCT in 10 umole of EPC-/a-T lipid) in the hindlimbs with a clearance half-life of about 55 hours showed detectable blood levels up to 70 hours. Thus, sCT-MLVs injected intramuscularly can achieve prolonged delivery to the systemic circulation.

EXAMPLE VII

Clearance of Lipid from the Site of Intramuscular Injection

The rate of clearance of lipid of a given liposome formulation was determined by monitoring the clearance of a radioactive lipid tracer ($^{125}$I-BPE) incorporated into the liposome from the injection site. The protocol of determination of clearance half-life was as described in Example III. The results are shown in FIG. 5. Semi-log plots of the percent radioactivity remaining at the injection site versus time of two formulations with identical llpid composition but were extruded to two different sizes (1.0 um and 0.2 um) are shown in FIG. 6. It is clear that the rate of lipid clearance from the injection site is similar to that of sCT clearance (i.e., at first order kinetics) and that the larger liposomes clear significantly slower than the smaller liposomes.

Table 5 summarizes the lipid clearance half-lives of several liposome formulations and compares them to the sCT clearance half-lives of $^{125}$I-sCT MLVs of identical composition and size.

TABLE 5

| Composition | Dose (umole lipid) | Clearance Half-Lives (hours) | |
|---|---|---|---|
|  |  | $^{125}$I-sCT-MLV | $^{125}$I-BPE-MLV |
| EPC/a-T | 2 | 25.9 | 58.4 |
| EPC/a-T | 10 | 55.4 | 110.7 |
| EPG/a-T | 10 | 8.6 | 17.7 |
| EPC/C/a-T | 10 | 69.5 | 138.3 |

As shown in the table, for a given liposome formulation, the lipid appeared to clear at about half the rate as the encapsulated drug, i.e., the half-life of clearance of the lipid was about double that of the corresponding sCT clearance from the site of injection. This implies that the drug and lipid are leaving the injection site by different mechanisms, i.e., the liposomes do not leave the injection site as an intact particle.

EXAMPLE VIII

Effect of Mixing sCT-MLVs with Empty MLV

Reverse evaporation vesicles composed of EPC/a-T encapsulating $^{125}$I-sCT and sCT were prepared according to a standard REV procedure as described by Szoka (1978). The vesicles were extruded through 0.4 and 0.2 micron polycarbonate filters and non-encapsulated sCT was removed from the liposomes by washing three times in PBS by centrifugation. The preparation was filtered through a sterile 0.22 micron filter.

Empty MLVs of the same composition were prepared and extruded through a one micron filter under sterile conditions as described in Example I. The REVs were mixed with the MLVs in a lipid mole ratio of 1:50 such that each IM injection contained about $1 \times 10^5$ cpm of $^{125}$I-sCT and about 0.5 ug of sCT in 10 mole umole of total lipid. The mixture of liposomes were allowed to stand overnight at 4° C. prior to injection into the rats. $^{125}$I-sCT-MLVs were prepared as described in Example I.

Rats were injected subcutaneously or intramuscularly with the liposome mixture as indicated in Table 6 or with $^{125}$I-sCT-REVs or $^{125}$I-sCT-MLVs containing about the same amount of sCT and about $1 \times 10^5$ cpm per injection as the mixture. The clearance of the $^{125}$I-radiolabel from the site ofinjection was followed as described in Example III. The clearance half-lives are shown in Table 6.

TABLE 6

| Liposome Sample | Type of Liposome (size in micron) | Lipid Dose (umole) | Half-Life (hours) |
|---|---|---|---|
| EXPT. (A): EPC/a-T |  |  |  |
| Small (drug) Liposomes | $^{125}$I-sCT-REV (0.20) | 0.3 | 7.2 |
| Mixture Small (drug) Empty Liposomes | $^{125}$I-sCT-REV + MLV (0.2 + 1.0) | 0.3 + 10 | 41.9 |
| Large (drug) Liposomes | $^{125}$I-SCT-MLV (1.0) | 10. | 55.4 |
| EXPT. (B): EPC/C/a-T |  |  |  |
| Small (drug) Liposomes | $^{125}$I-sCT-REV (0.2) | 0.16 | n.d. |

TABLE 6-continued

| Liposome Sample | Type of Liposome (size in micron) | Lipid Dose (umole) | Half-Life (hours) |
|---|---|---|---|
| Mixture Small (drug) | $^{125}$I-sCT-MLV + MLV (0.2 + 1.0) | 0.16 + 9.84 | 61.2 |
| Empty Liposomes Large (drug) | $^{125}$I-sCT-MLV (1.0) | 10. | 69.5 |
| Liposomes EXPT. (C): EPC/a-T | | | |
| Low Dose (drug) Liposomes | $^{125}$I-sCT-MLV (1.0) | 0.2 | 21.2 |
| Mixture (drug) Empty Liposomes | $^{125}$I-sCT-MLV + MLV (1.0) | 0.2 + 8.95 | 37.9 |
| Large Dose (drug) Liposomes | $^{125}$I-sCT-MLV (1.0) | 9.25 | 32.9 |

Type of liposomes were: the whole lipid dose (0.3 umole) made of small liposomes with encapsulated drug; the dose made of a mixture of 0.3 umoles of small liposomes with encapsulated drug and 10 umoles of empty liposomes; and the whole lipid dose of 10 umole made of large empty liposomes.

Figure 7:
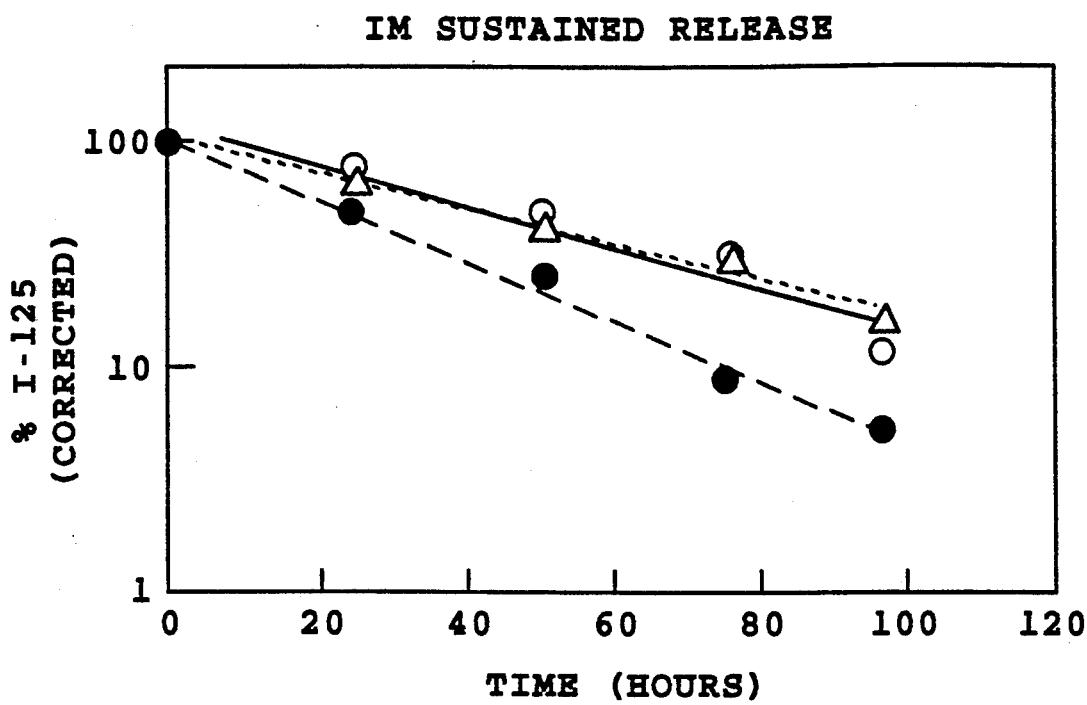
FIG. 7 is a semi-log plot of percent of $^{125}$I-sCT remaining at intramuscular injection site versus time. $^{125}$I-sCT-MLV at 9.25 umole lipid dose (open circles), $^{125}$I-sCT-MLV at 0.2 umole lipid dose (closed circles) and mixture of $^{125}$I-sCT-MLV at 0.2 umole lipid dose and empty MLV at 8.95 umole lipid dose (triangles).

From the data shown, it is obvious that the mixture of small drug loaded liposomes and large empty liposomes gave clearance kinetics similar to that of large sCT-MLVs at the same total lipid dose. The clearance half-life of $^{125}$I-sCT-REV in the experiment B was not determined but was estimated to be about 10 hours based on the low lipid dose and the small size of the formulation. The clearance half-lives of the mixture formulation and the homogeneously loaded liposome formulation were approximately the same. In experiment C, the mixture tested was composed ofliposomes of drug loaded liposomes of the same size as the empty liposomes. The semi-log plot of the clearance of the intramuscular site of injection was shown in FIG. 7. In this experiment, the student t-test (t=3.205) showed that there were significant differences between the low lipid dose $^{125}$I-sCT-MLV clearance rate and the high lipid dose $^{125}$I sCT-MLV and the mixture. There was no significant difference between the clearance rate of the high lipid dose $^{125}$I-sCT-MLV and the mixture (t=0.741). From these three experiments, it is clearly demonstrated that a prolonged release formulation of liposomes can be achieved by either making liposomes of defined size, composition and lipid dose which contain the drug in all the liposomes or as a mixture in which a small population of the liposomes contain the drug while the bulk of the formulation is composed of empty liposomes of either the same or preferably different size particle as the drug containing liposomes to make up the necessary lipid dose. Thus, the convenience of producing and processing a significantly smaller batch of drug containing liposomes for a much larger batch size final product to achieve the desired release kinetics as described in FIG. 1 can be achieved.

EXAMPLE IX

Biological Activity of Prolonged Release sCT-Liposomes Retrieved from Injection Site $^{125}$I-sCT-MLVs prepared as described in Example I were injected subcutaneously at 2 U (i.e., 0.5 ug) in 21 umole of total lipid per injection into the hindlimbs of Sprague-Dawley rats. Such a formulation had a clearance half-life of 84 tu 90 hours. At daily intervals, two rats were sacrificed and the radioactivity remaining in the limbs were determined as described in Example IV. Immediately after gamma counting, the skin of the limb was peeled back and the visible white pouch of the remaining sCT-MLVs at the injection site was collected by washing with ice cold phosphate buffered saline containing 1,000 K.I.U./ml of Trasylol (FBA Pharmaceuticals). The retrieved samples (usually about 30% of the remaining dose) and an aliquot of the original njection sample were frozen until the end of the seven day experiment. The hypocalcemic activities of the original and retrieved samples were determined by the bioassay as described in Example II. The expected sCT activity in mU was estimated based on the specific activity of the $^{125}$I-sCT in the encapsulation solution and the appropriate amount of the samples were lysed prior to injection into the rats for bioassay. The activity of the retrieved samples were expressed as a percentage of the original preparation which was treated similarly. As a control experiment, empty liposomes of the same dose and composition were also injected subcutaneously into rats. The samples were retrieved from the injection sites, frozen, treated as the $^{125}$I-sCT. MLV samples and injected into rats for bioassay. The results are summarized in Table 7.

TABLE 7

| Time After Injection (days) | % of Activity of Original Preparation | | |
|---|---|---|---|
| | sCT-MLV | | |
| | Expt. A | Expt. B | MLV Alone |
| Original | 100 | 100 | no detectable act. |
| 1 | 74 | 73 | not determined |
| 3 | 84 | 96 | no detectable act. |
| 5 | 84 | 69 | no detectable act. |
| 7 | 89 | 79 | no detectable act. |

The results showed that the liposomes themselves had no hypocalcemic activity. The sCT liposomes retrieved from the injection sites of the rats showed no significant progressive loss of biological activity. Therefore the drug which is released over a one week period from a prolonged release liposome formulation is biologically active.

EXAMPLE X

Clearance Kinetics of $^{125}$I-sCT.MLV Prepared by Solvent Injection Method

Oligolamellar liposomes encapsulating $^{125}$I-sCT are prepared by solvent injection as described in U.S. Pat. No. 4,752,425. Briefly, 50 ml of a solution composed of sCT and $^{125}$I-sCT in citrate buffered saline was prepared and the lipids composed of partially hydrogenated, (IV=40) egg phosphatidylchuline:cholesterol:atocopherol in molar ratios of 67:33:0.1 were d.ssolved in 50 ml of freon 11 at 400 umole lipids per ml. The lipid freon solution was injected slowly into the sCT solution with agitalion under vacuum at 20° C. Most of the freon was vaporized in the injection phase. The preparation was further stirred under high vacuum to remove the residual solvent. The liposomes formed were extruded through one micron pore size polycarbonate filter and the unencapsulated sCT was removed by centrifugation in buffered saline as described in Example I. The $^{125}$I-sCT-MLVs were then injected into rats as described in Example III to determine the clearance rate of the formulation.

TABLE 8

| Liposome Preparation Method | Liposome Composition | Lipid Dose (umole) | Clearance Half-Life (hours) |
|---|---|---|---|
| Expt. A | | | |
| Solvent Injection | EPC/C/a-T | 21 | 78.3 |
| Thin Film Hydration | EPC/C/a-T | 21 | 85.5 |
| Expt. B | | | |
| Solvent Injection | EPC/C/a-T | 23 | 113.2 |
| Thin Film Hydration | EPC/C/a-T | 22 | 103.4 |

From the clearance half-lives shown, there is no significant difference in the clearance times between the solvent injection prepared sCT liposomes versus the thin film hydration preparations of sCT liposomes.

EXAMPLE XI

Prolonged Release of Gentamicin from Gentamicin Liposomes

Gentamicin liposomes were prepared by solvent injection method as described in Example X. The encapsulation solution containing gentamicin at 100 to 200 mg/ml and the lipids composed of egg PC/EPG/a-T in molar ratios of 90:10:0.1 were dissolved in freon at 50 to 100 umole/ml. The gentamicin liposomes were washed in citrate buffered saline by centrifugation as described in Example III. The gentamicin concentration in the liposomes formulation was determined by the EMIT assay (Syva, Palo Alto, CA) after lysis in triton X-100.

Since gentamicin cannot be easily radiolabeled with $^{125}I$ without changing its physical interaction with lipids, the clearance half-life cannot be determined as described in the above examples for sCT. Gentamicin in circulation is known to be rapidly excreted in the urine. Therefore, the apparent absorption rate constant, $K_a$, was estimated with the urinary excretion.

Male Sprague-Dawley rats weighing 200 to 300 g injected intramuscularly with 0.4 to 0.5 ml of either free gentamicin solution or gentamicin liposomes. One group of four rats was immediately placed in metabolic cages (one rat per cage) and urine was collected at 24 hour intervals for the duration of the experiment. Cages were rinsed with distilled water after each collection and the volume of the pooled urine and rinses were recorded. An aliquot of each sample was frozen until assay.

Figure 8:
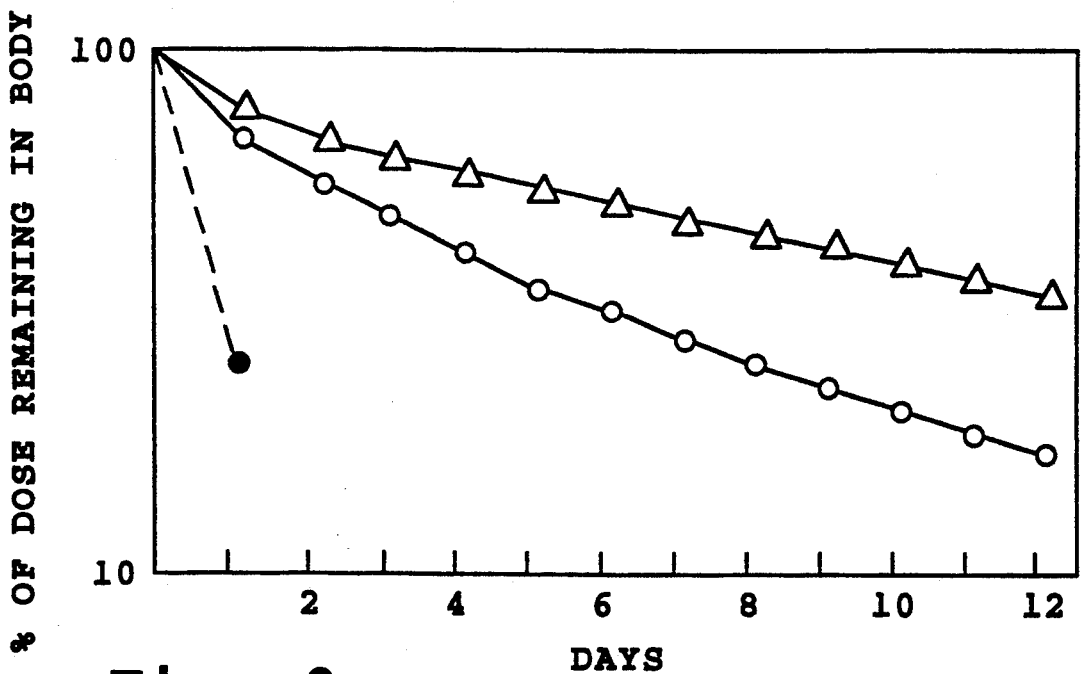
FIG. 8 Percent injected dose remaining in rats after receiving intramuscular injection of free gentamicin (dotted line) and two different gentamicin liposomes.

FIG. 8 showed a typical semi-log plot of the percent dose remaining in the body versus time after injection from which the apparent first order absorption constant, $K_a$, was calculated from the slope. The percent dose remaining in the body of rats which have received free gentamicin ranged from 25 to 30 percent as estimated from the amount of drug excreted in the urine. The gentamicin is gradually excreted in the next few days. In FIG. 8, data from rats which had received gentamicin liposomes with two different $K_a$ are shown (open triangle - $K_a$ is calculated to be 0.0032 per hour; open circle - $K_a$ is calculated to be 0.0070 per hour: closed circle data point illustrates the data from control rats after receiving free gentamicin).

TABLE 9

| Samples | Lipid Dose (umol/inj.) | Rate Const. $K_a$/hour |
|---|---|---|
| Gentamicin solution | 0 | 5.3 |
| Gentamicin liposomes | | |
| EPC/A-T = 99.9:0.1 | 53 | 0.0032 |
| EPC/EPG/a-T = 95:5:0.1 | 53 | 0.0070 |
| EPC/EPG/a-T = 95:5:0.1 | 129 | 0.0021 |

Table 9 shows apparent first order absorption rate constant of rate injected intramuscularly with gentamicin solution or gentamicin liposomes.

From the data, it is apparent that liposomal formulations of gentamicin decreased the absorption of gentamicin tremendously. In the formulations tested, the $K_a$ were decreased by three orders of magnitude, thus, demonstrating the prolonged absorption of gentamicin from gentamicin liposomes after IM administration.

What is calimed is:

1. A liposome composition for use in administering a liposome-impermeable compound to the bloodstream from an intramuscular or subcutaneous site of injection, comprising
    an aqueous suspension of liposomes containing the compound in entrapped form, and
    mixed with said suspension, empty liposomes, which do not contain the entrapped drug, having an average size and in an amount effective to produce up to a severalfold increase in the half-life of clearance of the liposome entrapped compound from such injection site compared with the clearance half-life of the liposome-entrapped compound in the absence of the empty liposomes.

2. A method of increasing the clearance half-life, as measured from the site of injection, of a liposome-impermeable compound injected into an intramuscular or subcutaneous injection site, in liposome entrapped form, cmoprising
    preparing a suspension of liposomes containing the compound in entrapped form,
    mixing the suspension of liposomes with empty liposomes, which do not contain the entrapped drug, selected to produce up to a severalfold increase in compound clearance half-life at the injection site, compared with the clearance half-life of the liposome-entrapped compound from the injection site in the absence of the empty liposomes, and
    injecting the mixed liposomes into the injection site.

3. The method of claim 2, wherein the compound is an antibiotic selected from the group consisting of gentamicin, amikacin, and doxorubicin.

4. The method of claim 2, which further includes reducing the mole percent of charged phospholipids in the liposomes to increase the clearance half-life of the compound from the site of injection relative to liposomes composed essentially of only charged lipids.

5. The method of claim 2, wherein the liposomes containing the entrapped drug have an average size of less than about 0.3 microns, and the average size of the injected liposomes is selectively increased by adding increasing amount of empty liposomes having an average size greater than about 0.5 micron.

6. The composition of claim 4, wherein the lipsomes contain between about 5-100 mole percent phosphatidylglycerol.

7. The composition of claim 2, wherein the liposomes of the compound-containing liposome suspension have average sizes less than about 0.3 microns.

8. The composition of claim 1, wherein the empty liposomes have an average particle size greater than about 0.5 micron.

9. The composition of claim 8, wherein the compound is a peptide selected from the group consisting of calcitonin, insulin, growth hormone, interferon, and interleukin-2.

10. The composition claim 1, wherein the compound is an antibiotic selected from the group consisting of gentamicin amikacin, and doxorubicin.

11. The composition of claim 1, wherein the liposomes include alpha-tocopherol, at a concentration of at least 0.2 mole percent.

12. The method of claim 2, wherein the compound is a peptide selected from the group consisting of calcitonin, growth hormone, insulin, interferon, and interleukin-2.

13. The method of claim 2, wherein the liposomes are composed of neutral lipids and further contain cholesterol at a mole ratio about 40%.

* * * * *